(12) United States Patent
Lee et al.

(10) Patent No.: US 12,016,976 B2
(45) Date of Patent: Jun. 25, 2024

(54) SUBMUCOSAL LIFTING COMPOSITIONS AND METHODS OF SAME

(71) Applicant: GI SUPPLY, Mechanicsburg, PA (US)

(72) Inventors: Patrick Lee, Long Grove, IL (US); Robert G. Whalen, Willington, CT (US); Ethan Krokonko, Harrisburg, PA (US); Amy A. Cameron, Union, CT (US); Erica A. Ward, Marysville, PA (US)

(73) Assignee: GI SUPPLY, Mechanicsburg, PA (US)

( * ) Notice: Subject to any disclaimer, the term of this patent is extended or adjusted under 35 U.S.C. 154(b) by 0 days.

(21) Appl. No.: 17/335,235

(22) Filed: Jun. 1, 2021

(65) Prior Publication Data
US 2021/0393859 A1    Dec. 23, 2021

Related U.S. Application Data

(60) Provisional application No. 63/042,836, filed on Jun. 23, 2020.

(51) Int. Cl.
*A61L 31/04* (2006.01)
*A61B 90/00* (2016.01)
*A61L 31/14* (2006.01)

(52) U.S. Cl.
CPC ............ *A61L 31/042* (2013.01); *A61B 90/02* (2016.02); *A61L 31/14* (2013.01); *A61L 2400/06* (2013.01)

(58) Field of Classification Search
CPC .... A61L 31/042; A61L 31/14; A61L 2400/06; A61L 31/16; A61L 2300/216; A61L 2300/442; A61L 31/145; A61B 90/02; C08L 1/26
See application file for complete search history.

(56) References Cited

U.S. PATENT DOCUMENTS

| 3,758,682 A * | 9/1973 | Huber | C12N 9/0089 |
| | | | 530/416 |
| 2003/0225460 A1 * | 12/2003 | Gostout | A61K 31/717 |
| | | | 623/23.72 |
| 2005/0002909 A1 * | 1/2005 | Moehlenbruck | A61P 43/00 |
| | | | 514/16.7 |
| 2007/0048251 A1 * | 3/2007 | Arthur | C09J 129/04 |
| | | | 424/78.37 |
| 2009/0069806 A1 * | 3/2009 | De La Mora Levy | |
| | | | A61B 17/072 |
| | | | 606/198 |
| 2011/0230438 A1 * | 9/2011 | Bos | A61K 31/728 |
| | | | 514/54 |
| 2012/0244108 A1 * | 9/2012 | Yang | A61K 31/765 |
| | | | 424/78.38 |
| 2020/0261355 A1 | 8/2020 | Morales Molina et al. | |

FOREIGN PATENT DOCUMENTS

| EP | 2537867 | * 12/2012 | ............ C08B 37/08 |
| EP | 3400930 A1 | 11/2018 | |
| WO | WO-2017/118774 A1 | 7/2017 | |

OTHER PUBLICATIONS

Gandhi and Mancera, Chem Biol Drug Des 2008; 72: 455-482 (Year: 2008).*
Castro et al., Solutions for submucosal injection: What to choose and how to do it World Journal of Gastroenterology, World Journal of Gastroenterology, Feb. 21, 2019; 25(7): 777-788. (Year: 2019).*
Uraoka et al., Effectiveness of glycerol as a submucosal injection for EMR, Gastrointestinal Endoscopy, 2005, vol. 61, No. 6, 736-740. (Year: 2005).*
International Application No. PCT/US2021/035081, International Search Report and Written Opinion, mailed Sep. 2, 2021.
DeAngelis et al., Chemoenzymatic synthesis of glycosaminoglycans: re-creating, re-modeling and re-designing nature's longest or most complex carbohydrate chains, Glycobiology, 23(7):764-77 (2013).
Miller et al., Molecular engineering of glycosaminoglycan chemistry for biomolecule delivery, Acta Biomater., 10(4):1705-19 (2014).

* cited by examiner

*Primary Examiner* — Aradhana Sasan

(74) *Attorney, Agent, or Firm* — MARSHALL, GERSTEIN & BORUN LLP

(57) ABSTRACT

Provided herein are submucosal lifting compositions and methods of using same. The submucosal lifting agents of the disclosure include a polysaccharide, a polyol, and a colorant.

31 Claims, 1 Drawing Sheet

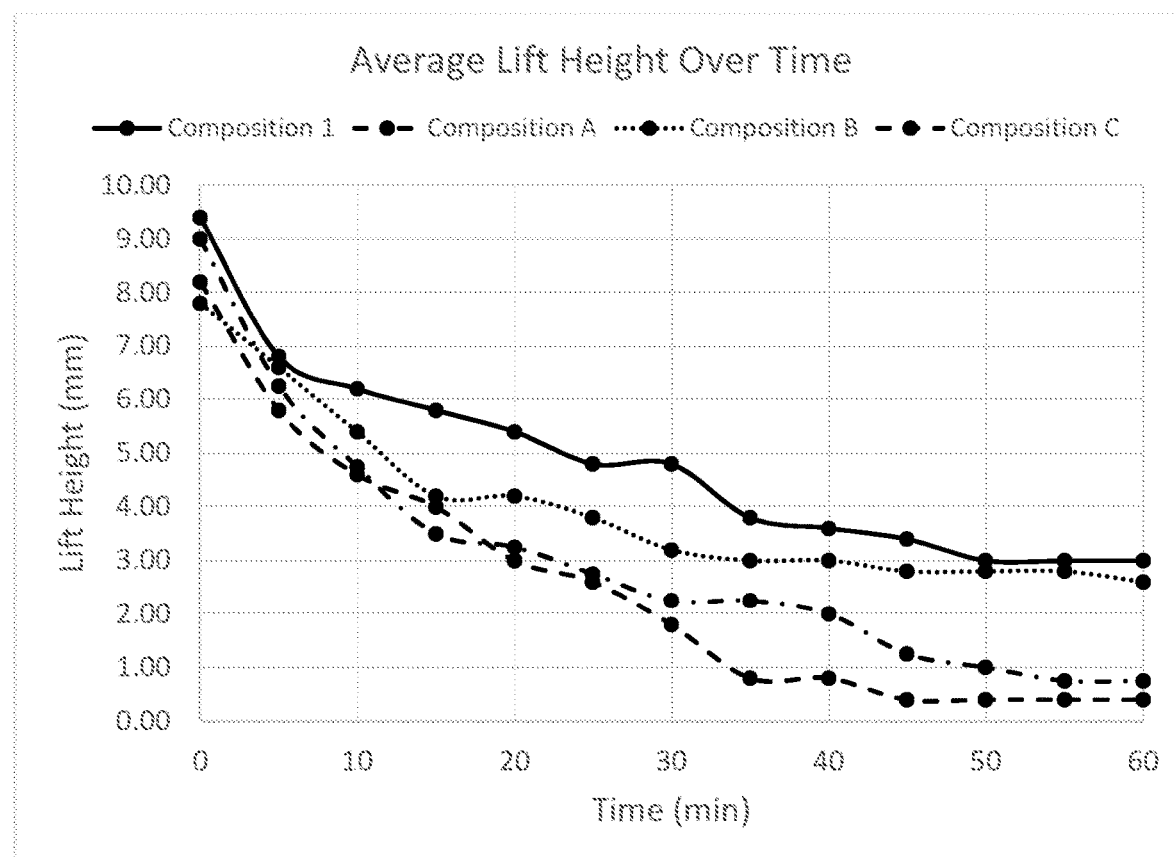

SUBMUCOSAL LIFTING COMPOSITIONS AND METHODS OF SAME

CROSS-REFERENCE TO RELATED APPLICATIONS

This application claims the benefit of the filing date of U.S. Provisional Application No. 63/042,836, filed Jun. 23, 2020, the disclosure of which is hereby incorporated by reference in its entirety.

BACKGROUND

An endoscope is a medical device that enables viewing of the interior of a body cavity or hollow organ without employing invasive surgical procedures. The endoscope includes a flexible elongated body (e.g., a tube) having a suitable imaging device at its distal end portion. The endoscope may be inserted through a naturally occurring opening, such as the esophagus or rectum, or through a small incision surgically made in the body. Suitable surgical instruments may be passed through the endoscope to perform various medical procedures, such as, for example, tissue sampling or removal of diseased tissue or polyps.

Endoscopic procedures are commonly used for diagnosis and/or treatment of the gastrointestinal (GI) tract. For example, an endoscopic procedure may be performed to take tissue samples from the GI tract for pathological evaluation and/or therapeutic purposes. For instance, with advances in the imaging technology, endoscopic procedures may be used to accurately detect and remove pre-cancerous mucosal tissue or tumors from various locations in the GI tract.

Interventional endoscopists perform various tasks including fluid-assisted polypectomy, endoscopic mucosal resection (EMR), and endoscopic submucosal dissection (ESD) procedures to remove pre-cancerous or cancerous mucosal tissue from the GI tract. Such fluid-assisted procedures may involve injecting a fluid cushion into submucosal tissue (e.g., cushioning) or injecting a fluid between target tissue layers (e.g., dissection) so as to lift or separate the target tissue layer in order to safely perform the procedure (e.g., by preventing or reducing risks of perforating the GI tract).

Injectable compositions, however, dissipate and therefore may not raise or separate the target tissue layer for the entire duration of the procedure. If the fluid is dissipated, the endoscopist must re-inject the fluid to assure the target tissue layer remains raised or bulked. The more times the tissue is pierced with an injection needle to inject the fluid, the more holes that are created for the fluid to leak out.

SUMMARY

Provided herein are submucosal lifting compositions comprising a polysaccharide present in an amount ranging from about 0.05 wt % to 0.5 wt %, based on the total weight of the composition, a polyol present in an amount ranging from about 10 wt % to 20 wt % based on the total weight of the composition, and a colorant present in an amount ranging from about 0.0001 wt % to 0.005 wt % based on the total weight of the composition.

The disclosure further provides a sealed and sterile syringe comprising the composition according to the disclosure.

Also provided are methods of lifting a submucosa, comprising injecting the composition of the disclosure into a submucosa of a subject, thereby providing a lifted submucosa having a first lift height.

Further provided are methods of gastrointestinal submucosal resectioning, comprising injecting the composition of the disclosure to a gastrointestinal submucosal tissue of a subject to lift the tissue to a first lift height, thereby providing a lifted gastrointestinal submucosal tissue, and surgically resecting the lifted gastrointestinal submucosal tissue.

Further aspects and advantages will be apparent to those of ordinary skill in the art from a review of the following detailed description. While the compositions and methods are susceptible to embodiments in various forms, the description hereafter includes specific embodiments with the understanding that the disclosure is illustrative and is not intended to limit the disclosure to the specific embodiments described herein.

BRIEF DESCRIPTION OF THE DRAWINGS

FIG. 1 is a graph showing the average lift height of a submucosa over time for compositions according to the disclosure and three comparative compositions.

DETAILED DESCRIPTION

Provided herein are submucosal lifting compositions and methods of using the same. The compositions of the disclosure provide one or more advantages including, but not limited to, requiring a lower injection force than commercially available lifting agents, delayed dispersion within the submucosa relative to commercially available lifting agents, and/or substantially maintained lift height over time (e.g. retains at least about 50% of the first lift height after about 30 minutes following injection).

Submucosal Lifting Composition

In embodiments, the disclosure provides submucosal lifting compositions including a polysaccharide present in an amount ranging from about 0.05% (w/v) to about 0.5% (w/v), a polyol present in an amount ranging from about 10% (w/v) to about 20% (w/v), and a colorant present in an amount ranging from about 0.0001% (w/v) to about 0.005% (w/v). In embodiments, the disclosure provides submucosal lifting compositions including a polysaccharide present in an amount ranging from about 0.05 wt % to about 0.5 wt % based on the total weight of the composition, a polyol present in an amount ranging from about 10 wt % to about 20 wt % based on the total weight of the composition, and a colorant present in an amount ranging from about 0.0001 wt % to about 0.005 wt % based on the total weight of the composition.

The compositions disclosed herein include a polysaccharide. The polysaccharide can include linear polysaccharides, such as cellulose, amylose, pectin, alginates, and derivatives thereof, including alkyl cellulose polymers such as methyl cellulose (MC), hydroxyalkyl celluloses such as hydroxypropyl cellulose (HPC) and hydroxypropylmethyl cellulose (HPMC), and carboxyalkyl celluloses and their salts including carboxymethyl celluloses (CMC). Counterions for use in carboxyalkyl celluloses include Group I cations such as sodium and potassium, Group II cations such as magnesium and calcium, and mixtures of the foregoing.

Polysaccharides for use in the compositions of the disclosure can also include glycosaminoglycans, preferably non-sulfated glycosaminoglycans such as hyaluronic acid and its salts, desulfated heparin, desulfated chondroitin sulfate and desulfated dermatan sulfate. Hyaluronic acid and its salts (also called hyaluronan, hyaluronate or HA) are anionic, nonsulfated glycosaminoglycans. HA is distributed widely throughout connective, epithelial, and neural tissues.

Counterions for use in hyaluronic acid salts include Group I cations such as sodium and potassium, Group II cations such as magnesium and calcium, and mixtures of the foregoing.

Polysaccharides for use in the compositions of the disclosure also include polysaccharides comprising a main chain and a plurality of monosaccharide side groups. Examples of such compounds include galactomannans which are polysaccharides having a mannose backbone with galactose side groups e.g., a (1-4)-linked beta-D-mannopyranose backbone with branch points from their 6-positions linked to alpha-D-galactose (i.e., 1-6-linked alpha-D-galactopyranose), such as guar gum, fenugreek gum, tara gum, locust bean gum and carob gum. Polysaccharides for use in conjunction with the present disclosure also include polysaccharides comprising a main chain and a plurality of oligosaccharide side groups (where "oligosaccharide" is defined herein as polysaccharide chains of 2, 3, 4, 5, 6, 7, 8, 9 or 10 saccharide groups), including xanthan gum.

Polysaccharides can further include branch-on-branch polysaccharides such as amylopectin, gum arabic, arabinoxylan, among others.

In embodiments, the polysaccharide is selected from the group consisting of methylcellulose (MC), hydroxypropylcellulose (HPC), hydroxypropylmethylcellulose (HPMC), hydroxycellulose, hydroxyethylcellulose (HEC), carboxymethylcellulose (CMC), hyaluronic acid, desulfated heparin, desulfated chondroitin sulfate, desulfated dermatan sulfate, guar gum, fenugreek gum, tara gum, locust bean gum, carob gum, amylopectin, gum Arabic, arabinoxylan, any salt thereof, and any combination thereof. In embodiments, the polysaccharide comprises hydroxyethylcellulose. In embodiments, the polysaccharide includes methylcellulose (MC), hydroxypropylcellulose (HPC), hydroxypropylmethylcellulose (HPMC), hydroxycellulose, hydroxyethylcellulose (HEC), carboxymethylcellulose (CMC), or a combination thereof. In some embodiments, the polysaccharide includes hydroxyethylcellulose, hydroxypropylcellulose, dextran, guar gum, or any combination thereof.

The polysaccharide can generally be present in the composition in any amount. Without intending to be bound by theory, it is believed that as the amount of polysaccharide decreases, the amount of time the initial lift is maintained when the composition is provided to a tissue decreases and the faster the composition will disperse within the submucosa of a subject. Further, without intending to be bound by theory, it is believed that as the amount of polysaccharide increases, the viscosity of the composition will generally increase, and thus more force will be required to pass the composition through a syringe needle or a smaller gauge needle (i.e., a needle with higher diameter) will be required. In embodiments, the polysaccharide can be present in the composition in an amount ranging from about 0.05% (w/v) to about 0.5% (w/v), from about 0.1% (w/v) to about 0.5% (w/v), from about 0.15% (w/v) to about 0.45% (w/v), or from about 0.2% (w/v) to about 0.3% (w/v), for example about 0.05, 0.075, 0.1, 0.15, 0.2, 0.25, 0.3, 0.35, 0.4, 0.45, or 0.5% (w/v). In embodiments, the polysaccharide can be present in the composition in an amount ranging from about 0.05 wt % to about 0.5 wt %, from about 0.1 wt % to about 0.5 wt % from about 0.15 wt % to about 0.45 wt %, or from about 0.2 wt % to about 0.3 wt %, for example about 0.05, 0.075, 0.1, 0.15, 0.2, 0.25, 0.3, 0.35, 0.4, 0.45, or 0.5 wt %, based on the total weight of the composition. The advantageous lift and resistance to dispersion demonstrated by the compositions of the disclosure does not increase appreciably if the polysaccharide is provided at a concentration above 0.5% (w/v) or about 0.5 wt %. Rather, it will be understood that the maximum limit on the amount of polysaccharide is a functional limit based on the limitations of the end use (e.g., gauge of needle, desired flow rate, etc.).

The polysaccharide can be present in any suitable form, e.g., a powder, an aqueous solution, etc. Addition of the polysaccharide to water generally increases the viscosity of the water. In some cases, the polysaccharide can be defined by its viscosity. The viscosity of the polysaccharide is generally defined by the viscosity of a 1% or 2% aqueous solution of the polysaccharide in water at 25° C. In embodiments, the polysaccharide has a viscosity ranging from about 500 cP to about 10,000 cP, about 1000 cP to about 9000 cP, about 2500 cP to about 7500 cP, about 4000 cP to about 6000 cP, for example about 500, 750, 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, or 10,000 cP.

The compositions disclosed herein include a polyol. In embodiments, the polyol can be included to help reduce the surface tension of the composition. Advantageously, the polyol can be included to help emulsify and disperse the polysaccharide in the composition, and protect the polysaccharide during sterilization. The polyol can include, but is not limited to, glycerin, diglycerin, propylene glycol, dipropylene glycol, butanediol, pentanediol, butylene glycol, ethylene glycol, diethylene glycol, triethylene glycol, or any combination thereof. In embodiments, the polyol includes glycerin or diglycerin. In some embodiments, the polyol includes glycerin.

Without intending to be bound by theory, it is believed that the polyol helps to emulsify and protect the polysaccharide in the composition. The polyol can also help to reduce the surface tension of the composition. The polyol can be included in the composition in an amount ranging from about 10% (w/v) to about 20% (w/v), about 12% (w/v) to about 18% (w/v), or about 15% (w/v) to about 17% (w/v), for example about 10, 11, 12, 13, 14, 15, 16, 17, 18, 19, or 20% (w/v). Based on the total weight of the composition, the polyol can be included in the composition in an amount ranging from about 10 wt % to about 20 wt %, about 12 wt % to about 18 wt %, or about 15 wt % to about 17 wt %, for example about 10, 11, 12, 13, 14, 15, 16, 17, 18, 19, or 20 wt %. When the polyol is present in amounts below about 10% (w/v) or about 10 wt %, the surface tension of the composition is high, requiring in increased injection force and/or a smaller gauge needle (i.e., a needle with a higher diameter) to inject the composition into the submucosa. Without intending to be bound by theory, while it is believed that increasing the amount of polyol above 20% (w/v) or 20 wt % can provide additional protection to the polysaccharide in the composition, it is expected that the amount of additional protection provided will have little effect on the properties of the final composition and, further, it is believed that the likelihood of dispersion of the lift composition in the submucosa increases as the amount of polyol in the composition increases above 20% (w/v).

The compositions disclosed herein further include a colorant. The colorant can be included to visually mark the submucosa for resection by a surgeon. The colorant can include, but is not limited to, methylene blue, isosulfan blue, indocyanin green, fluorescein, rose bengal, gentian violet, or any combination thereof.

The colorant can be included in the composition in an amount ranging from about 0.0001% (w/v) to about 0.005% (w/v), about 0.0005% (w/v) to about 0.004% (w/v), or about 0.001% (w/v) to about 0.003% (w/v), for example about 0.0005, 0.0006, 0.0007, 0.0008, 0.0009, 0.001, 0.0015, 0.002, 0.0025, 0.003, 0.0035, 0.004, 0.0045, or 0.005% (w/v). Based on the total weight of the composition, the colorant can be included in an amount ranging from about 0.0001 wt % to about 0.005 wt %, about 0.0005 wt % to about 0.004 wt %, or about 0.001 wt % to about 0.003 wt %, for example about 0.0005, 0.0006, 0.0007, 0.0008, 0.0009, 0.001, 0.0015, 0.002, 0.0025, 0.003, 0.0035, 0.004, 0.0045, or 0.005 wt %. Generally, the colorant is included in an amount sufficient to mark the targeted submucosa, but not to obscure the field of view of the resecting surgeon. Advantageously, the compositions described herein can dye and/or mark the targeted submucosa at lower levels of colorant than current commercial products.

In embodiments, the polysaccharide includes hydroxyethylcellulose, the polyol includes glycerin, and the colorant includes methylene blue.

The composition can further include a number of suitable excipients and/or carriers. Examples of suitable excipients and/or carriers include, but are not limited to, a preservative, a buffer, and water.

Examples of suitable preservatives include, but are not limited to, benzyl alcohol, methylparaben, ethylparaben, benzalkonium chloride, or combinations thereof. The composition can include a preservative in an amount up to about 4.0% (w/v), or about 4.0 wt %, based on the total weight of the composition. For example, in embodiments, the preservative can be included in an amount ranging from about 0% (w/v) to about 4.0% (w/v), about 0.01% (w/v) to about 4.0% (w/v), about 0.05% (w/v) to about 2.0% (w/v), about 0.075% (w/v) to about 1.5% (w/v), or about 0.5% (w/v) to about 1.0% (w/v). In embodiments, the preservative can be included in an amount ranging from about 0 wt % to about 4.0 wt %, about 0.01 wt % to about 4.0 wt %, about 0.05 wt % to about 2.0 wt %, about 0.075 wt % to about 1.5 wt %, or about 0.5 wt % to about 1.0 wt %, based on the total weight of the composition. In embodiments, the preservative includes benzyl alcohol. In embodiments, the preservative includes benzyl alcohol in an amount of about 1 wt %, based on the total weight of the composition.

In embodiments, the composition includes sterile water for injection (WFI). The water can be included in an amount of about 50 wt % to about 90 wt %, about 60 wt % to about 85 wt %, about 70 wt % to about 85 wt %, or about 75 wt % to about 80 wt %, for example about 50, 65, 70, 75, 80, 85 or 90 wt %, based on the total weight of the composition.

Suitable buffers can include, but are not limited to, phosphate buffered saline (PBS), tris(hydroxymethyl)aminomethane (Tris), tris-buffered saline, 4-(2-hydroxyethyl)-1-piperazineethanesulfonic acid (HEPES), HEPES-buffered saline, sodium phosphate dibasic anhydrous, potassium phosphate monobasic anhydrous, and any combination thereof. In embodiments, the buffer comprises sodium phosphate dibasic anhydrous and potassium phosphate monobasic anhydrous. The buffer can be included in any amount sufficient to achieve an appropriate in vivo pH at the target site. In embodiments, the buffer is present in an amount of about 0.01 wt % to about 0.25 wt %, about 0.05 wt % to about 0.2 wt %, about 0.1 to about 0.2 wt %, or about 0.15 to about 0.2 wt %, for example about 0.01, 0.05, 0.1, 0.15, 0.2, or 0.25 wt %, based on the total weight of the composition. In embodiments, the buffer comprises sodium phosphate dibasic anhydrous and potassium phosphate monobasic anhydrous in a total amount of about 0.16 wt %, based on the total weight of the composition. In embodiments, the composition has a pH ranging from about 5.5 to about 8.0, about 6.0 to about 7.5, or about 6.5 to about 7.0, for example about 5.5, 6.0, 6.5, 7.0, 7.5 or 8.0.

The compositions according to the disclosure can be sterile. The compositions can also be non-pyrogenic. In some cases, each component of the composition is sterilized. That is, each component can be subjected to sterilization conditions (e.g., autoclaving, filter sterilization, ionizing radiation) prior to being added to the composition. Alternatively, or additionally, the composition can be terminally sterilized. For example, the composition can be prepared by combining the sterilized or unsterilized components, and subsequently sterilized (e.g. autoclaved, filter sterilized, exposed to ionizing radiation) once the final composition is prepared. Additionally, the composition can be sterilized before and/or after it is packaged in, for example, a syringe. The method of sterilization can generally depend on the components of the composition. For example, autoclaving is generally not suitable for compositions containing non-heat stable components (e.g. HPMC, non-crosslinked hyaluronic acid, xanthan gum, pectin, etc.).

In embodiments, the composition of the disclosure is an aqueous solution. In embodiments, the composition is not an emulsion.

The composition of the disclosure can have a viscosity ranging from about 5 cP to about 150 cP, about 25 cP to about 150 cP, about 50 cP to 150 cP, about 75 cP to about 150 cP, about 100 cP to about 150 cP, about 110 cP to about 140 cP, about 100 cP to about 120 cP, about 5.0 cP to about 15 cP, about 7.5 cP to about 12.5 cP, or about 8 cP to about 12 cP, for example about 5, 5.5, 6, 6.5, 7, 7.5, 8, 8.5, 9, 9.5, 10, 10.5, 11, 11.5, 12, 12.5, 13, 13.5, 14, 14.5, 15, 25, 30, 35, 40, 45, 50, 55, 60, 65, 70, 75, 80, 85, 90, 95, 100, 105, 110, 115, 120, 125, 130, 135, 140, 145, or 150 cP. In embodiments, the composition has a viscosity of about 100 cP to about 125 cP, such as about 110 cP or about 112 cP. When the viscosity of the composition is below about 5.0 cP, the composition can disperse more quickly within the submucosa, resulting in a lower lift and a shorter duration of the lift. When the viscosity of the composition is greater than about 150 cP, then the injection force required to inject the composition into a submucosa is greater. Alternatively, or additionally, when the viscosity of the composition is greater than about 150 cP, a needle having a smaller gauge (i.e., a needle having a higher diameter) may be required in order to suitably inject the composition to the submucosa. As reported herein, viscosity measurements are obtained at ambient room temperature (i.e., about 20° C. or about 25° C.), using a Brookfield DV-E Viscometer at an RPM (i.e., rotations per minute) of 12.

The compositions of the disclosure can have a density of about 1.0 g/mL to about 1.3 g/mL, for example about 1.0 g/mL to about 1.2 g/mL, about 1.0 g/mL to about 1.1 g/mL to about 1.0 g/mL to about 1.05 g/mL, for example about 1.0, 1.01, 1.02, 1.03, 1.04, 1.05, 1.06, 1.07, 1.08, 1.09, 1.1, 1.2, or 1.3 g/mL. In embodiments, the composition has a density of about 1.02 g/mL. In embodiments the composition has a density of about 1.03 g/mL. The density can be determined by measuring the weight of a particular volume of the composition under ambient conditions (about 20-25° C.), and dividing that weight by the particular volume (e.g., the weight of a 2 mL sample in grams divided by 2 mL).

The compositions described herein can be packaged in any packaging suitable for storage and/or delivery of the composition to the submucosa. For example, in embodiments, the composition can be loaded into a syringe, where it can be terminally sterilized, sealed, and stored until use. The syringe typically includes a barrel having an opening to receive a plunger at its proximal end and having a fitting at its distal tip for direct or indirect engagement with an injection needle, such that the interior of the syringe barrel is placed in fluid communication with the interior of the injection needle.

The size and diameter of the barrel of syringe is not particularly limited, and can generally have a volume ranging from about 5 cc to about 50 cc, about 10 cc to about 40 cc, or about 20 cc to about 30 cc, for example about 5, 7.5, 10, 12.5, 15, 20, 25, 30, 40, or 50 cc.

Similarly, the size, or gauge, of the needle is not particularly limited and can be selected based on the ultimate properties of the specific submucosa lifting composition, as well as the desired injection parameters (e.g., injection force, flow rate, etc.). For example, the viscosity of the composition and the size (or gauge) of the needle of the syringe, can be selected and tailored in order to achieve an acceptable injection force and/or flow rate. One example of a suitable needle is a Carr-Locke 25 ga injection needle, having a 5 mm needle length and a 230 cm working length, available from US Endoscopy. Another example of a suitable needle is a 23 ga Interject Needle, having a 4 mm needle length and a 240 cm working length, available from Boston Scientific. Other suitable needle gauges can be from 20 ga to 27 ga, for example 20, 21, 22, 23, 24, 25, 26, or 27 ga. In embodiments, the injection force is applied constantly (for the duration of the injection) and can range from about 4.00 lbF (17.8 N) to about 7.00 lbF (31.1 N), for example about 4.00, 4.50 lbF (20.0 N), 5.00 lbF (22.2 N), 5.25 lbF (23.4 N), 5.50 lbF (24.5 N), 5.75 lbF (25.6 N), 6.00 lbF (26.7 N), 6.50 lbF (28.9 N), or 7.00 lbF. In embodiments, the injection force is applied constantly at about 5.25 lbF and provides a flow rate of at least about 0.100 mL/s using a 23 ga injection needle, having a 4 mm needle length and a 240 cm working length. In embodiments, the viscosity of the composition and the syringe are configured such that the injection flow rate is at least about 0.05 mL/s, as described in more detail, below.

The compositions of the disclosure can be stored and maintain stability for at least about 1 year, at least about 2 years, or at least about 3 years after sterilization and packaging, for example for about 1, 2, 3, 4, or 5 years after sterilization and packaging. The compositions are generally stable at ambient room temperature, that is, from about 20° C. to about 25° C.

Methods of Use

The disclosure further provides methods of using the composition described herein.

In embodiments, the disclosure provides a method of lifting a submucosa including injecting the composition of the disclosure into a submucosa of a subject, thereby providing a lifted submucosa having a first lift height.

The disclosure also provides methods of gastrointestinal submucosal resectioning including injecting the composition of the disclosure to a gastrointestinal submucosal tissue of a subject to lift the tissue to a first lift height, thereby providing a lifted gastrointestinal submucosal tissue, and surgically resecting (using, e.g., a snare, knife, biopsy forceps, scissors, etc.) the lifted gastrointestinal submucosal tissue.

As used herein, the term "first lift height" refers to the change in the height of the submucosa from prior to injection of the composition to immediately after injection of the composition. That is, the first lift height is measured relative to the height of the submucosa prior to injecting the composition. In embodiments, the first lift height is at least about 2.0 mm. The first lift height can depend, for example, on the type of submucosa, and the size of the area to be lifted, etc.

In embodiments, the first lift height can range from about 2.0 mm to about 11.0 mm, about 4.0 mm to about 10.0 mm, or about 6.0 mm to about 8.0 mm, for example, about 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, or 11.0 mm, as measured relative to the height of the submucosa prior to injecting.

In embodiments, the method includes injecting the composition in an amount sufficient to lift the tissue to a first lift height of about 2.0 mm. For example, the method can include injecting the composition in an amount sufficient to lift the tissue to a first lift height in a range of about 2.0 mm to about 11.0 mm, about 4.0 mm to about 10.00 mm, or about 6.0 mm to about 8.0 mm. The amount of the composition required to lift the tissue to the first lift height can depend, in part, on the type of submucosal tissue and/or the desired size (e.g. lift height and/or lift diameter) of the lifted submucosa. The amount sufficient to lift the tissue is within the purview of the person of ordinary skill in the art, e.g., the resecting surgeon. In embodiments, the method includes injecting from about 5 mL to about 50 mL, about 5 to about 40 mL, about 10 mL to about 35 mL, about 15 mL to about 30 mL, or about 20 to about 25 mL of the composition to a patient, for example about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 6, 47, 48, 49, or 50 mL.

In embodiments, the methods include injecting the composition at a flow rate of at least 0.05 mL/s. As provided above, the flow rate can be varied depending on the final viscosity of the composition, the size or gauge of the needle, and/or the injection force applied to the syringe. The flow rate can range from about 0.05 mL/s to about 0.20 mL/s, about 0.05 mL/s to about 0.15 mL/s, for example, about 0.05, 0.075, 0.10, 0.125, 0.15, 0.175, or 0.20 mL/s. In embodiments, the flow rate is at least about 0.10 mL/s/

Advantageously, the compositions and methods of the disclosure can provide a lifted submucosa that retains at least 50% of the first lift height after 30 minutes following injection, for example 50%, 55%, 60%, 65%, 70%, 75%, 80%, 85%, 90%, 95%, or 100% of the first lift height after 30 minutes following injection. Without intending to be bound by theory, it is believed that due to the unexpected synergy between the polyol and polysaccharide, the composition of the disclosure disperses more slowly from the injection site, providing a localized and lasting lift to the submucosa.

In embodiments, the composition is injected to a submucosa of a subject. In embodiments, the subject is a mammal, for example, a human. The composition can be injected to any submucosa of the subject, for example, a submucosa of the gastrointestinal, respiratory, or genitourinary tracts. The composition of the disclosure is particularly suitable for use in lifting a submucosal tissue of the gastrointestinal (GI) tract. In embodiments, the submucosal tissue includes a lesion, such as, for example, a polyp, an adenoma, an early-stage cancer, and/or any combination thereof.

The foregoing description is given for clearness of understanding only, and no unnecessary limitations should be understood therefrom, as modifications within the scope of the disclosure may be apparent to those having ordinary skill in the art.

The compositions and methods in accordance with the disclosure can be better understood in light of the following examples, which too, are merely intended to illustrate the compositions and methods, and are not meant to limit the scope thereof in any way.

EMBODIMENTS

Specifically contemplated embodiments of the disclosure are herein described in the following numbered paragraphs. These embodiments are intended to be illustrative in nature and not intended to be limiting.

[1] A submucosal lifting composition comprising:
 a polysaccharide present in an amount ranging from about 0.05% (w/v) to about 0.5% (w/v) or about 0.05 wt % to about 0.5 wt %, based on the total weight of the composition;
 a polyol present in an amount ranging from about 10% (w/v) to about 20% (w/v), or about 10 wt % to about 20 wt %, based on the total weight of the composition; and,
 a colorant present in an amount ranging from about 0.0001% (w/v) to about 0.005% (w/v), or about 0.0001 wt % to about 0.005 wt %, based on the total weight of the composition.

[2] The composition of paragraph [2], wherein the polysaccharide is selected from the group consisting of methylcellulose (MC), hydroxypropylcellulose (HPC), hydroxypropylmethylcellulose (HPMC), hydroxycellulose, hydroxyethylcellulose (HEC), carboxymethylcellulose (CMC), hyaluronic acid, desulfated heparin, desulfated chondroitin sulfate, desulfated dermatan sulfate, guar gum, fenugreek gum, tara gum, locust bean gum, carob gum, amylopectin, gum Arabic, arabinoxylan, any salt thereof, and any combination thereof.

[3] The composition of paragraph [1] or [2], wherein the polysaccharide comprises methylcellulose (MC), hydroxypropylcellulose (HPC), hydroxypropylmethylcellulose (HPMC), hydroxycellulose, hydroxyethylcellulose (HEC), carboxymethylcellulose (CMC), or a combination thereof.

[4] The composition of any one of paragraphs [1]-[3], wherein the polysaccharide comprises hydroxyethylcellulose.

[5] The composition of any one of paragraphs [1]-[4], wherein the polysaccharide has a viscosity ranging from about 500 cP to about 10,000 cP.

[6] The composition of any one of paragraphs [1]-[5], wherein the polyol is selected from the group consisting of glycerin, diglycerin, propylene glycol, dipropylene glycol, butanediol, pentanediol, butylene glycol, ethylene glycol, diethylene glycol, triethylene glycol, and any combination thereof.

[7] The composition of any one of paragraphs [1]-[6], wherein the polyol comprises glycerin or diglycerin.

[8] The composition of any one of paragraphs [1]-[7], wherein the polyol comprises glycerin.

[9] The composition of any one of paragraphs [1]-[8], wherein the colorant is selected from the group consisting of methylene blue, isosulfan blue, indocyanin green, fluorescein, rose bengal, gentian violet, and any combination thereof.

[10] The composition of any one of paragraphs [1]-[9], wherein the colorant comprises methylene blue.

[11] The composition of any one of paragraphs [1]-[10], further comprising one or more of water, preservative, and buffer.

[12] The composition of paragraph [11], wherein the composition comprises sterile water for injection (WFI).

[13] The composition of any one of paragraphs [1]-[12], wherein the composition is sterile.

[14] The composition of paragraph [13], wherein each of the components of the composition is sterilized.

[15] The composition of paragraph [13] or [14], wherein the composition is terminally sterilized.

[16] The composition of any one of paragraphs [1]-[15], wherein the composition is an aqueous solution.

[17] The composition of any one of paragraphs [1]-[16], wherein the composition is not an emulsion.

[18] The composition of any one of paragraphs [1]-[17], wherein the composition has a viscosity ranging from about 5.0 cP to about 150 cP.

[19] The composition of any one of paragraphs [1]-[18], wherein the composition has a pH ranging from about 5.5 to about 8.0.

[20] The composition of any one of paragraphs [1]-[19], wherein the polysaccharide comprises hydroxyethylcellulose, the polyol comprises glycerin, and the colorant comprises methylene blue.

[21] A sealed and sterile syringe comprising the composition of any one of paragraphs [1]-[20].

[22] A method of lifting a submucosa, comprising:
 injecting the composition of any one of paragraphs [1]-[20] into a submucosa of a subject, thereby providing a lifted submucosa having a first lift height.

[23] The method of paragraph [22], wherein the first lift height is at least about 2.0 mm, and is measured relative to the height of the submucosa prior to injecting the composition.

[24] The method of paragraph [22]-[23], wherein the first lift height is in a range of about 2.0 mm to about 11.0 mm, and is measured relative to the height of the submucosa prior to injecting the composition.

[25] The method of any one of paragraphs [22]-[24], wherein the lifted submucosa retains at least 50% of the first lift height after 30 minutes.

[26] The method of any one of paragraphs [22]-[25], wherein the subject is a mammal, e.g. a human.

[27] The method of any one of paragraphs [22]-[26], comprising injecting the composition at a flow rate of at least 0.05 mL/s.

[28] The method of any one of paragraphs [22]-[27], wherein the submucosa comprises a submucosal tissue of the gastrointestinal tract.

[29] The method of paragraph [28], wherein the submucosal tissue comprises a lesion.

[30] The method of paragraph [29], wherein the lesion is selected from the group consisting of a polyp, an adenoma, an early-stage cancer, and any combination thereof.

[31] A method of gastrointestinal submucosal resectioning, the method comprising:
 injecting the composition of any one of paragraphs [1]-[20] to a gastrointestinal submucosal tissue of a subject to lift the tissue to a first lift height, thereby providing a lifted gastrointestinal submucosal tissue; and,
 surgically resecting the lifted gastrointestinal submucosal tissue.

[32] The method of paragraph [31], wherein the composition is injected in an amount sufficient to lift the tissue to the first lift height.

[33] The method of paragraph [31] or [32], wherein the first lift height is at least about 2.0 mm, and is measured relative to the height of the gastrointestinal submucosal tissue prior to injecting the composition.

[34] The method of any one of paragraphs [31]-[33], wherein the lifted gastrointestinal submucosal tissue retains at least 50% of the first lift height after 30 minutes.

[35] The method of any one of paragraphs [31]-[34], wherein the subject is a mammal, e.g. a human.

EXAMPLES

Example 1—Ex Vivo Lift Retention

A composition according to the disclosure (Composition 1) was prepared and compared to two commercial submucosal lifting compositions (Compositions A and B), as well as a saline control (Composition C). Composition 1 was a composition according to the disclosure including about 0.125% (w/v) (about 0.120 wt %) hydroxyethylcellulose, about 19% (w/v) (about 18.131 wt %) glycerin, and about 0.001% (w/v) (about 0.001 wt %) methylene blue. Composition 1 further included water for injection (WFI), a preservative, and a buffer in amounts according to the disclosure. The hydroxyethylcellulose of Composition 1 had a 1% solution viscosity of about 5000 cP. The final viscosity of Composition 1 was about 100-120 cP, as measured according to the disclosure.

Composition A was commercial product Eleview® supplied by Aries Pharmaceuticals, Inc. Eleview® is an emulsion consisting of water for injection, medium chain triglycerides, Polaxamer 188, polyoxy-15-hydroxystearate, sodium chloride, and methylene blue.

Composition B was commercial product ORISE™ Gel supplied by Boston Scientific. ORISE™ Gel is a viscous gel solution.

Composition C was a 0.9% saline solution.

A volume of 3.0±0.2 mL of each composition was injected. The width and height of the lifted submucosa were measured and recorded immediately after injection. The width was observed to be dependent on the particular tissue as opposed to the composition itself. The height of the lifted submucosa, relative to the pre-lift height of the submucosa prior to injection (e.g., pre-lift height=0 mm), was then measured every 5 minutes for a total of 60 minutes. The height of the submucosa immediately after injection (i.e., at time=0) is the first lift height, as described by the disclosure. Each composition was tested a total of five times. The lift heights as measured over time can be seen in Table 1, below, and FIG. 1.

TABLE 1

Ex vivo Lift Height (mm) After Injection

| Composition | Time (min) | Trial 1 | Trial 2 | Trial 3 | Trial 4 | Trial 5 | Average |
|---|---|---|---|---|---|---|---|
| 1 | 0 | 6 | 8 | 6 | 14 | 13 | 9.40 |
|   | 5 | 4 | 6 | 4 | 11 | 9 | 6.80 |
|   | 10 | 4 | 4 | 4 | 11 | 8 | 6.20 |
|   | 15 | 3 | 4 | 3 | 11 | 8 | 5.80 |
|   | 20 | 3 | 4 | 3 | 11 | 6 | 5.40 |
|   | 25 | 3 | 4 | 2 | 9 | 6 | 4.80 |
|   | 30 | 3 | 4 | 2 | 9 | 6 | 4.80 |
|   | 35 | 2 | 4 | 1 | 9 | 3 | 3.80 |
|   | 40 | 2 | 3 | 1 | 9 | 3 | 3.60 |
|   | 45 | 1 | 3 | 1 | 9 | 3 | 3.40 |
|   | 50 | 1 | 2 | 1 | 8 | 3 | 3.00 |
|   | 55 | 1 | 2 | 1 | 8 | 3 | 3.00 |
|   | 60 | 1 | 2 | 1 | 8 | 3 | 3.00 |
| A | 0 | 10 | 7 | 10 | 9 | 6 | 9.00 |
|   | 5 | 9 | 5 | 5 | 6 | 4 | 6.25 |
|   | 10 | 8 | 3 | 3 | 5 | 4 | 4.75 |
|   | 15 | 6 | 2 | 2 | 4 | 1 | 3.50 |
|   | 20 | 5 | 2 | 2 | 4 | 1 | 3.25 |
|   | 25 | 4 | 1 | 2 | 4 | 0 | 2.75 |
|   | 30 | 4 | 1 | 1 | 3 | 0 | 2.25 |
|   | 35 | 4 | 1 | 1 | 3 | 0 | 2.25 |
|   | 40 | 4 | 1 | 0 | 3 | 0 | 2.00 |
|   | 45 | 3 | 1 | 0 | 1 | 0 | 1.25 |
|   | 50 | 3 | 0 | 0 | 1 | 0 | 1.00 |
|   | 55 | 3 | 1 | 0 | 0 | 0 | 0.75 |
|   | 60 | 3 | 0 | 0 | 0 | 0 | 0.75 |
| B | 0 | 8 | 7 | 10 | 7 | 7 | 7.80 |
|   | 5 | 6 | 5 | 10 | 6 | 6 | 6.60 |
|   | 10 | 6 | 4 | 8 | 5 | 4 | 5.40 |
|   | 15 | 4 | 3 | 6 | 4 | 4 | 4.20 |
|   | 20 | 4 | 3 | 6 | 4 | 4 | 4.20 |
|   | 25 | 3 | 3 | 6 | 4 | 3 | 3.80 |
|   | 30 | 2 | 3 | 6 | 3 | 2 | 3.20 |
|   | 35 | 2 | 3 | 5 | 3 | 2 | 3.00 |
|   | 40 | 2 | 3 | 5 | 3 | 2 | 3.00 |
|   | 45 | 2 | 3 | 4 | 3 | 2 | 2.80 |
|   | 50 | 2 | 3 | 4 | 3 | 2 | 2.80 |
|   | 55 | 2 | 3 | 4 | 3 | 2 | 2.80 |
|   | 60 | 2 | 3 | 4 | 2 | 2 | 2.60 |
| C | 0 | 10 | 6 | 5 | 9 | 11 | 8.20 |
|   | 5 | 8 | 5 | 1 | 6 | 9 | 5.80 |
|   | 10 | 6 | 4 | 0 | 5 | 8 | 4.60 |
|   | 15 | 6 | 4 | 0 | 4 | 6 | 4.00 |
|   | 20 | 6 | 3 | 0 | 4 | 2 | 3.00 |
|   | 25 | 3 | 3 | 0 | 4 | 0 | 2.60 |
|   | 30 | 0 | 3 | 0 | 3 | 0 | 1.80 |
|   | 35 | 0 | 2 | 0 | 2 | 0 | 0.80 |
|   | 40 | 0 | 2 | 0 | 2 | 0 | 0.80 |
|   | 45 | 0 | 0 | 0 | 2 | 0 | 0.40 |
|   | 50 | 0 | 0 | 0 | 2 | 0 | 0.40 |
|   | 55 | 0 | 0 | 0 | 2 | 0 | 0.40 |
|   | 60 | 0 | 0 | 0 | 2 | 0 | 0.40 |

Table 2, below, demonstrates the average retention (%) of the lift height over time for each of the tested compositions. Lift height retention was measured according to the following equation (1):

$$h_L = \frac{h_x}{h_0} \times 100\% \qquad (1)$$

wherein $h_L$ is the percent retention (%) of the first lift height, $h_0$ is the average first lift height (at t=0) (mm), and $h_x$ is the lift height (mm) at each given time.

TABLE 2

Average Lift Height Retention (%)

| Composition | Time (min) | | | | | | | | | | | | |
|---|---|---|---|---|---|---|---|---|---|---|---|---|---|
| | 0 | 5 | 10 | 15 | 20 | 25 | 30 | 35 | 40 | 45 | 50 | 55 | 60 |
| 1 | 100 | 72.3 | 66.0 | 61.7 | 57.4 | 51.1 | 51.1 | 40.4 | 38.3 | 36.2 | 31.9 | 31.9 | 31.9 |
| A | 100 | 69.4 | 52.8 | 38.9 | 36.1 | 30.6 | 25.0 | 25.0 | 22.2 | 13.9 | 11.1 | 8.3 | 8.3 |
| B | 100 | 84.6 | 69.2 | 53.8 | 48.7 | 41.0 | 38.5 | 38.5 | 35.9 | 35.9 | 35.9 | 35.9 | 33.3 |
| C | 100 | 70.7 | 56.1 | 48.8 | 36.6 | 31.7 | 22.0 | 9.8 | 9.8 | 4.9 | 4.9 | 4.9 | 4.9 |

As shown in Tables 1 and 2, and FIG. 1, the composition according to the disclosure not only had a higher first lift height (9.40 mm), but was also able to retain the lift for a longer period of time. At fifteen minutes following injection, Composition 1 was the only composition having a greater than 60% retention of the first lift height. Thirty minutes following injection, Composition 1 retained 51.1% of the first lift height, on average, as compared to 25.0%, 38.5% and 22.0% of the average first lift height for Compositions A, B, and C, respectively. Although Composition B maintained almost 85% of the first lift height after 5 minutes, as shown in Table 1, Composition B provided no advantages over Composition 1 at this time point, as the lift height of each of these compositions was between about 6.5 and 7 mm.

Accordingly, Example 1 demonstrates that the composition according to the disclosure can advantageously provide an equivalent, if not better submucosal lift, while retaining that lift for a longer period of time, relative to commercially available products.

What is claimed is:

1. A submucosal lifting composition comprising:
   a polysaccharide present in an amount ranging from about 0.05 wt % to about 0.5 wt %, based on the total weight of the composition;
   a polyol present in an amount ranging from about 10 wt % to about 20 wt %, based on the total weight of the composition; and
   a colorant present in an amount ranging from about 0.0001 wt % to 0.005 wt %, based on the total weight of the composition, wherein the submucosal lifting composition does not include a glycosaminoglycan,
   wherein, when the submucosal lifting composition is injected into a submucosal tissue, the submucosa is lifted to a height of at least 3 mm for 60 minutes, relative to the pre-lift height of the submucosa prior to injection.

2. The composition of claim 1, wherein the polysaccharide is selected from the group consisting of methylcellulose (MC), hydroxypropylcellulose (HPC), hydroxypropylmethylcellulose (HPMC), hydroxycellulose, hydroxyethylcellulose (HEC), carboxymethylcellulose (CMC), desulfated dermatan sulfate, guar gum, fenugreek gum, tara gum, locust bean gum, carob gum, amylopectin, gum Arabic, arabinoxylan, any salt thereof, and any combination thereof.

3. The composition of claim 1, wherein the polysaccharide comprises hydroxyethylcellulose.

4. The composition of claim 1, wherein the polysaccharide has a viscosity ranging from about 500 cP to about 10,000 cP.

5. The composition of claim 1, wherein the polyol is selected from the group consisting of glycerin, diglycerin, propylene glycol, dipropylene glycol, butanediol, pentanediol, butylene glycol, ethylene glycol, diethylene glycol, triethylene glycol, and any combination thereof.

6. The composition of claim 1, wherein the polyol comprises glycerin.

7. The composition of claim 1, wherein the colorant is selected from the group consisting of methylene blue, isosulfan blue, indocyanin green, fluorescein, rose bengal, gentian violet, and any combination thereof.

8. The composition of claim 1, wherein the colorant comprises methylene blue.

9. The composition of claim 1, further comprising one or more of water, preservative, and buffer.

10. The composition of claim 1, wherein the composition is sterile.

11. The composition of claim 10, wherein each of the components of the composition is sterilized.

12. The composition of claim 10, wherein the composition is terminally sterilized.

13. The composition of claim 1, wherein the composition is an aqueous solution.

14. The composition of claim 1, wherein the composition is not an emulsion.

15. The composition of claim 1, wherein the composition has a viscosity ranging from about 5.0 cP to about 150 cP.

16. The composition of claim 1, wherein the composition has a pH ranging from about 5.5 to about 8.0.

17. The composition of claim 1, wherein the polysaccharide comprises hydroxyethylcellulose, the polyol comprises glycerin, and the colorant comprises methylene blue.

18. A sealed and sterile syringe comprising the composition of claim 1.

19. A method of lifting a submucosa, comprising:
   injecting the composition of claim 1 into a submucosa of a subject, thereby providing a lifted submucosa having a first lift height.

20. The method of claim 19, wherein the first lift height is at least about 2.0 mm, and is measured relative to the height of the submucosa prior to injecting the composition.

21. The method of claim 19, wherein the first lift height is in a range of about 2.0 mm to about 11.0 mm, and is measured relative to the height of the submucosa prior to injecting the composition.

22. The method of claim 19, wherein the lifted submucosa retains at least 50% of the first lift height after 30 minutes.

23. The method of claim 19, comprising injecting the composition at a flow rate of at least 0.05 mL/s.

24. The method of claim 19, wherein the submucosa comprises a submucosal tissue of the gastrointestinal tract.

25. The method of claim 24, wherein the submucosal tissue comprises a lesion.

26. The method of claim 25, wherein the lesion is selected from the group consisting of a polyp, an adenoma, an early-stage cancer, and any combination thereof.

27. A method of gastrointestinal submucosal resectioning, the method comprising:

injecting the composition of claim 1 to a gastrointestinal submucosal tissue of a subject to lift the tissue to a first lift height, thereby providing a lifted gastrointestinal submucosal tissue; and, surgically resecting the lifted gastrointestinal submucosal tissue.

28. The method of claim 27, wherein the composition is injected in an amount sufficient to lift the tissue to the first lift height.

29. The method of claim 27, wherein the first lift height is at least about 2.0 mm, and is measured relative to the height of the gastrointestinal submucosal tissue prior to injecting the composition.

30. The method of claim 1, wherein the lifted gastrointestinal submucosal tissue retains at least 50% of the first lift height after 30 minutes.

31. A submucosal lifting composition consisting of:
- a polysaccharide present in an amount ranging from about 0.05 wt % to about 0.5 wt %, based on the total weight of the composition, wherein the polysaccharide is selected from the group of methylcellulose (MC), hydroxypropylcellulose (HPC), hydroxypropylmethylcellulose (HPMC), hydroxycellulose, hydroxyethylcellulose (HEC), carboxymethylcellulose (CMC), desulfated heparin, desulfated chondroitin sulfate, desulfated dermatan sulfate, guar gum, fenugreek gum, tara gum, locust bean gum, carob gum, amylopectin, gum Arabic, arabinoxylan, a salt of any of the foregoing, and any combination of the foregoing;
- a polyol present in an amount ranging from about 10 wt % to about 20 wt %, based on the total weight of the composition;
- a colorant present in an amount ranging from about 0.0001 wt % to 0.005 wt %, based on the total weight of the composition;
- a preservative;
- a buffer; and
- water;

wherein, when the submucosal lifting composition is injected into a submucosal tissue, the submucosa is lifted, relative to the submucosa prior to injection.

* * * * *

UNITED STATES PATENT AND TRADEMARK OFFICE
CERTIFICATE OF CORRECTION

PATENT NO. : 12,016,976 B2
APPLICATION NO. : 17/335235
DATED : June 25, 2024
INVENTOR(S) : Patrick Lee et al.

It is certified that error appears in the above-identified patent and that said Letters Patent is hereby corrected as shown below:

In the Claims

At Column 14, Line 17, "indocyanin green," should be -- indocyanine green, --.

At Column 15, Line 4, "and," should be -- and --.

At Column 15, Line 14, "claim 1," should be -- claim 27, --.

Signed and Sealed this
Tenth Day of December, 2024

Katherine Kelly Vidal
*Director of the United States Patent and Trademark Office*